United States Patent
Manke et al.

(10) Patent No.: US 6,880,034 B2
(45) Date of Patent: Apr. 12, 2005

(54) MEDICAL DEVICE WITH DUAL COMMUNICATIONS BUS

(75) Inventors: Joachim Manke, Loehnberg (DE); Peter Scheunert, Neunkirchen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 222 days.

(21) Appl. No.: 10/247,350

(22) Filed: Sep. 20, 2002

(65) Prior Publication Data

US 2003/0046439 A1 Mar. 6, 2003

Related U.S. Application Data

(63) Continuation of application No. PCT/EP01/03107, filed on Mar. 19, 2001.

(30) Foreign Application Priority Data

Mar. 20, 2000 (DE) .......................................... 100 13 665

(51) Int. Cl.[7] .............................................. G06F 13/36
(52) U.S. Cl. ...................................... 710/306; 710/316
(58) Field of Search ........................ 710/100, 305–306, 710/316; 714/25, 30, 43; 210/739; 604/4.01

(56) References Cited

U.S. PATENT DOCUMENTS

| | | | |
|---|---|---|---|
| 4,695,944 A | | 9/1987 | Zandveld et al. |
| 4,897,784 A | | 1/1990 | Nay |
| 5,618,441 A | * | 4/1997 | Rosa et al. ................. 210/739 |
| 5,620,608 A | * | 4/1997 | Rosa et al. ................. 210/739 |
| 5,629,871 A | * | 5/1997 | Love et al. .................. 702/34 |
| 5,784,547 A | * | 7/1998 | Dittmar et al. ............... 714/4 |
| 6,052,752 A | * | 4/2000 | Kwon ........................ 710/306 |
| 6,137,776 A | * | 10/2000 | Bauerschmidt et al. ..... 370/216 |
| 6,151,298 A | * | 11/2000 | Bernhardsson et al. ..... 370/225 |
| 6,676,621 B1 | * | 1/2004 | Menninger ................ 604/4.01 |

FOREIGN PATENT DOCUMENTS

| | | |
|---|---|---|
| DE | 40 22 365 | 1/1991 |
| DE | 198 49 787 | 2/2000 |
| EP | 0 306 211 | 3/1988 |
| EP | 0 491 183 | 6/1992 |
| GB | 2 282 244 | 3/1995 |
| WO | 99/66407 | 12/1999 |

* cited by examiner

Primary Examiner—Paul R. Myers
(74) Attorney, Agent, or Firm—Jacobson Holman PLLC

(57) ABSTRACT

A medical appliance having an auxiliary computer system in addition to its action computer system, and further having two communications buses. The auxiliary computer system independently monitors the functional mode of the action computer system and can induce a reliable state of the appliance in an emergency. To easily, quickly and reliably implement a programming, the execution of test sequences, the diagnosis and the maintenance of such an appliance, a connection line, which can be interrupted by a switch, is arrange between the communication buses, and both communications buses can be connected to form a unified communications bus via the communication line. A method for executing such a programming process, testing process, diagnostic process and/or maintenance process of a medical appliance is also provided.

19 Claims, 1 Drawing Sheet

MEDICAL DEVICE WITH DUAL COMMUNICATIONS BUS

This is a continuation of PCT/EP01/03107, filed Mar. 19, 2001 and published in German.

BACKGROUND OF THE INVENTION

1. Field of the Invention

The invention relates to a medical device having at least two units for monitoring and/or controlling thereof, and two communications buses. The units include at least one computer with a microprocessor, and at least one unit having a second computer with a second microprocessor, with each of the computers being attached to either the first or the second communications bus. The invention is also directed to a method for the programming, the implementation of the test sequences, the diagnosis and maintenance of such a device.

2. Description of the Related Art

Such medical devices often exhibit a computer architecture with two communications buses. Such a computer architecture is generally appropriate when, in addition to the action computer system, a medical device needs for safety requirements an auxiliary computer system that monitors independently the operating mode of the action computer system and in the event of an emergency can induce a safer state of the device.

Such a device is described in the German patent DE 198 49 787 C1, to whose publication reference is explicitly made here. In this patent application a hemodialysis unit is described that—based on the computer system—exhibits a modular construction. An operating unit, a hydraulic unit and a functional unit respectively include one action and one auxiliary computer each.

The action computers are connected by means of an action bus; the auxiliary computers, by means of an auxiliary bus. Furthermore, communication between the action and the auxiliary computer within one unit is possible.

The auxiliary computer of the operating unit of the hemodialysis unit exhibits an external interface. By means of this interface it is possible to conduct by means of an external device the programming, the implementation of test sequences, the diagnosis and the maintenance of all computers of the hemodialysis unit. However, the computer architecture of this device exhibits the following drawback. Whereas the auxiliary computers can be addressed relatively easily by means of the auxiliary bus, the action computers can be addressed only by means of the modular internal interface between an action computer and the related auxiliary computer. Not until after such a transition can the data be sent via the action bus. The internal computer connection turns out to be a bottleneck with respect to the data transfer rate, resulting in unnecessary long periods for data communications.

However, there are also objections of a different kind against modular internal communication. If data are to be transferred to an action computer, then it is necessary for the aforementioned reasons to use at least in one unit the modular internal interface between an action computer and the related auxiliary computer. Hence, several computers are always tied into the data transfer operation. Furthermore, each computer must have additional software to even handle the data transfer. In this respect the operation is altogether time consuming and error prone.

The DE-A-37 36 712 describes a similar modular-like dialysis unit, which provides a hierarchical computer structure. All control processors are connected to a main control processor, and all monitor processors are connected to a main monitor processor. The main processors in turn are interconnected.

The EP 0 491 183 A1 discloses a device, wherein the driver and receiver units are connected between a main data bus and an internal bus. To access the internal bus from the main data bus for test purposes, there are bidirectional logic means, which exhibit, however, a complicated design.

The EP 0 306 211 A2 describes a very expensive, synchronized twin computer system. To coordinate the cycles and the parallel running programs, there is data communications between two computer systems via its own controller.

The DE 40 22 365 A1 proposes a data transfer system, wherein an address bus and a data bus between a microprocessor and a data memory can be interrupted for the purpose of more efficient direct memory access (DMA).

An external device for diagnosis of an integrated switching circuit by means of a bus system is the subject matter of the GB 2 282 244 A.

SUMMARY OF THE INVENTION

The object of the invention is to improve in such a manner a generic medical device that a simple, fast and reliable programming operation, test sequence run, diagnosis and/or maintenance of the end devices, located at the two buses, are possible.

According to the teaching of the invention, this problem is solved with a medical device having at least two units for monitoring and/or controlling thereof, and two communications buses. The units include at least one computer with a microprocessor, and at least one unit having a second computer with a second microprocessor, with each of the computers being attached to either the first or the second communications bus. A connecting line is provided, which can be interrupted by a switch and by means of which the two communications buses can be connected to form a uniform communications bus.

With the aid of the system, according to the invention, it is possible to connect the two communications buses, whenever an external device for programming, for implementing test sequences, for diagnosis and/or for maintenance is supposed to be connected to the system, in order to form a uniform communications bus, with the result that simple, fast and more reliable connecting paths are provided that can be separated again safely and reliably after these process steps.

It is also conceivable that the programming, the implementation of the test sequences, the diagnosis and/or maintenance is conducted internally in the system by means of a computer in the medical device. In this case the method is analogous.

The switch is designed expediently as a relay switch. However, other switches, enabling a uniform connection between the two communications buses, can also be used.

In an especially advantageous embodiment, the connecting line can be interrupted with two switches connected in series. In this respect the one switch can be actuated by a computer, connected to the first communications bus; and the other switch can be actuated by a computer, connected to the second communications bus.

In another embodiment there are means for mode identification that exclude a connection of the communications buses whenever the medical device exercises its actual function in the sense of a medical application, for example during hemodialysis treatment. In this embodiment for connecting the two communications buses the device must be expediently in a special mode provided to this end. This feature is supposed to guarantee that the safety concept of the medical device, which is designed around the two separated communications buses, cannot be circumvented. The means for mode identification constitute advantageously part of the programming of the participating computers that drive the switch(es).

To connect to an external device, the medical device can exhibit an interface directly at one of the two communications buses, at one of the computers or—in the case of a connecting line with two switches—in the connecting line between the two switches. In the latter case the result is an especially reliable run when connected to an external device, because each computer system, which is connected by means of a communications bus, can actuate for itself whether it wants to be connected to the external device.

The external device can be realized by means of another computer or a computer network, wherein the connection can comprise a local connection or an intranet or internet connection.

Detector means that check the switch state and report to one of the computers can be provided.

The system, according to the invention, uses advantageously addressing techniques that maintain its uniqueness in the event of the bus connection.

In an especially advantageous embodiment of the invention, CAN buses are used as the communications buses.

In another embodiment of the invention, at least two units of the medical device exhibit one action and one auxiliary computer each. In this case the action computers are connected together by means of the first communications bus; and the auxiliary computers are connected together by means of the second communications bus.

In a preferred embodiment the medical device is a blood treatment device. High safety demands are made on such a device, which exhibits as a rule an extracorporeal blood circulation, where blood is taken from a patient or a donor and returned again. For this reason such a device also exhibits a complex design.

Examples of blood treatment procedures are blood cleaning by means of dialysis and/or filtration, by means of adsorption or by means of centrifugation.

The DE 198 49 787 C1 describes one basic design of a medical device to be used for the invention. The dialysis unit that is presented has an operating unit for data input and output, a hydraulic unit for supplying and draining the dialysis fluid and the ultrafiltrate as well as a functional unit for controlling the extracorporeal blood circulation. Each unit exhibits an action and an auxiliary computer, where the action computers are connected together by means of a first bus; and the auxiliary computers are connected together by means of a second bus.

However, such a dialysis unit can also be provided for hemofiltration, where the hydraulic unit assumes the task of providing substitution fluid, instead of providing dialysis fluid. The same applies to a hemodiafiltration unit, which enables hemodialysis and hemofiltration at the same time in order to combine the advantages of the treatment efficiency of both methods.

The invention is also based on the problem of providing a method for a simple fast and reliable programming, test, diagnosis and/or maintenance operation of a generic medical device with an interface to an external device.

The problem is solved in that for this purpose an external device is attached to the interface provided to this end; the two communications buses are connected to form one uniform communications bus; the programming, test, diagnostic and/or maintenance operation is conducted by means of an external device; and after completion of the programming, test, diagnostic and/or maintenance operation, the communications buses are separated again.

DESCRIPTION OF THE FIGURE

Other details and advantages of the invention are described in detail with reference to one embodiment presented in the drawing.

DETAILED DESCRIPTION OF THE PREFERRED EMBODIMENTS

Figure 1:
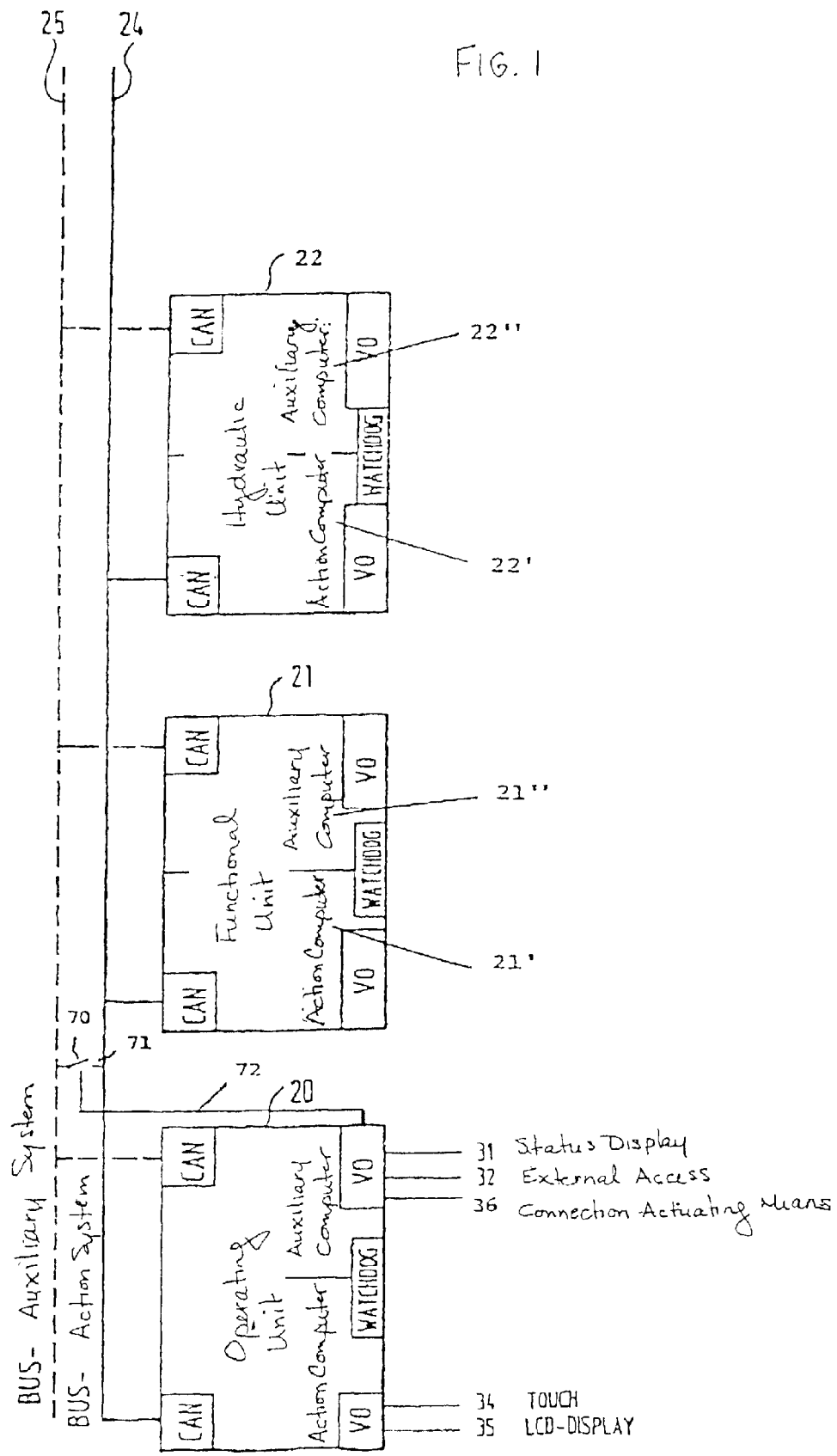
FIG. 1 depicts a computer structure of a hemodialysis unit, according to the invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

FIG. 1 depicts the computer structure of a hemodialysis unit, according to DE 198 49 787 C1. To the extent that it is not absolutely necessary for understanding the invention, the actuators and sensors of the individual units were omitted for the sake of a better overview. However, such details are disclosed in the DE 198 49 787 C1.

The computer structure of the hemodialysis machine exhibits an operating unit 20 with an action computer 20' with a touch screen 34 as the input means and an LCD display 35 as the output means. Furthermore, the operating unit contains an auxiliary computer 20", to which is connected a status display 31, an external access 32 and connection actuating means 36.

A functional unit 21 also comprises an action computer 21' and an auxiliary computer 21". These computers control and monitor the extracorporeal blood circulation of the hemodialysis unit. The hydraulic unit 22, which regulates and monitors the preparation, the inflow and outflow of the dialysis fluid and the ultrafiltration, is also divided into an action computer 22' and an auxiliary computer 22".

The action computers 20', 21', and 22' are connected together by means of a bus "action system" 24; and the auxiliary computers 20", 21" and 22" are connected together by means of a bus "auxiliary system" 25. Furthermore, there is a connecting line 71 for connecting the buses 24 and 25, which can be connected or interrupted with a relay switch 70.

The relay switch 70 is connected by means of a line 72 to the auxiliary computer 20" of the operating unit 20. If at this stage a programming, test, diagnostic and/or maintenance operation for the entire system or parts of the system is supposed to begin, then the user actuates the connection actuating means 36. The programming of the auxiliary computer 20" comprises means (which are not shown in detail) for mode identification, which determine the state of the hemodialysis machine and release the connection actuating means 36 only when the hemodialysis machine is in a suitable service mode, but not during dialysis treatment. In the latter case the separation of the buses 24 and 25 shall be maintained for safety reasons.

Following actuation of the connection actuating means 36, the auxiliary computer 20' sends a signal on the line 72, to close the relay switch 70. The operation that is introduced at this stage can be verified to the user by means of the status display 31.

An external device, which is attached to the external access 32, has now direct access to all computers of the units 20, 21 and 22 by means of the CAN interface 73 of the auxiliary computer 20', because the buses 24 and 25 are connected together.

If the programming, test, diagnostic and/or maintenance operation has ended, then the switch 70 is opened again by means of the connection activating means 36; and the connecting line 71 is interrupted. In this manner the action and auxiliary system can continue their actual independent function separately.

In FIG. 1 the connection 71 is shown symbolically at an arbitrary point of the buses 24 and 25. Depending on the bus system that is used, the expert is acquainted with the circumstances, how separations and connections can be carried out in existing bus lines—optionally in consideration of the load resistance—without affecting the bus functions.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A medical device comprising:
   at least two units for monitoring and/or controlling the medical device, said units including at least one computer with a microprocessor, and at least one unit having a second computer with a second microprocessor;
   first and second communications buses, with each of the computers being attached to either the first or the second communications bus; and
   a connecting line extending between the first and second communications buses which can be interrupted by a switch and by which the two communications buses can be connected to form a uniform communications bus.

2. The medical device, as claimed in claim 1, wherein the switch is a relay switch.

3. The medical device, as claimed in claim 1, wherein the switch can be actuated by one of the computers.

4. The medical device, as claimed in claim 1, wherein the connecting line can be interrupted by two switches connected in series.

5. The medical device, as claimed in claim 4, wherein one of the switches is actuated by a computer, connected to the first communications bus; and the other switch is actuated by a computer, connected to the second communications bus.

6. The medical device, as claimed in claim 1, wherein, upon mode identification, the first and the second communications bus are connected together by the switch only when the device is in a special mode provided to this end.

7. The medical device, as claimed in claim 1, wherein the first and second communications buses are CAN buses.

8. The medical device, as claimed in claim 1, wherein both communications buses use addressing techniques that allow unambiguous addressing of the computers and their components when the communications buses are connected together.

9. The medical device, as claimed in claim 1, wherein one of the communications buses includes an interface for connecting to an external device.

10. The medical device, as claimed in claim 1, wherein one of the computers includes an interface for connecting to an external device.

11. The medical device, as claimed in claim 4, further comprising an interface to an external device in the connecting line between the two switches.

12. The medical device, as claimed in claim 10, wherein individual computers or all computers of the medical device can be programmed, tested, diagnosed and/or maintenanced using the external device.

13. The medical device, as claimed in claim 1, wherein each of said at least two units includes an action computer and an auxiliary computer.

14. The medical device, as claimed in claim 13, wherein the action computers are connected together by the first communications bus and the auxiliary computers are connected together by the second communications bus.

15. The medical device, as claimed in claim 1, wherein the medical device is a blood treatment device.

16. The medical device, as claimed in claim 15, wherein the blood treatment device is a hemodialysis, hemofiltration or hemodiafiltration device.

17. The medical device, as claimed in claim 16, wherein the units include an operating unit for data input and output, a hydraulic unit for supplying and draining biological fluids and a functional unit for controlling an extracorporeal blood circulation.

18. A method for implementing a programming, test, diagnosis and/or maintenance operation of a medical device, the device having at least two units for monitoring and/or controlling thereof which include at least one computer with a microprocessor each, and where at least one unit contains a second computer with a second microprocessor, the device further having two communications buses, where each of the computers is attached to either the first or the second communications bus, and an interface to an external device, which is attached to one of the computers or one of the communications buses, said method comprising the steps of:
   attaching an external device to the interface;
   connecting the two communications buses to form a uniform communications bus;
   carrying out the programming, test, diagnostic and/or maintenance operation using the external device; and
   separating the communications buses upon completion of the programming, test, diagnostic and/or maintenance operation.

19. The method as claimed in claim 18, wherein prior to connecting the two communications buses, a mode of the medical device is identified; and the connection is rendered a function of whether the device is in a special state for carrying out the programming, test, diagnostic and/or maintenance operation.

* * * * *